United States Patent [19]
Hayes

[11] 4,003,955
[45] Jan. 18, 1977

[54] DEHYDROCYCLIZATION WITH AN ACIDIC MULTIMETALLIC CATALYTIC COMPOSITE

[75] Inventor: John C. Hayes, Palatine, Ill.

[73] Assignee: UOP Inc., Des Plaines, Ill.

[22] Filed: Mar. 8, 1976

[21] Appl. No.: 664,458

Related U.S. Application Data

[63] Continuation-in-part of Ser. No. 490,171, July 19, 1974, Pat. No. 3,948,762.

[52] U.S. Cl. .......................... 260/673.5; 208/139; 208/143; 252/442; 252/466 B; 260/673
[51] Int. Cl.$^2$ ............... C07C 3/04; C10G 23/04; B01J 27/08; B01J 23/62
[58] Field of Search .................... 260/673.5, 673; 208/139

[56] References Cited

UNITED STATES PATENTS

| | | | |
|---|---|---|---|
| 2,500,146 | 3/1950 | Fleck et al. | 260/668 D |
| 2,911,357 | 11/1959 | Myers et al. | 208/138 |
| 3,210,296 | 10/1965 | Gray | 260/466 PT |
| 3,825,487 | 7/1974 | Wilhelm | 208/139 |
| 3,840,471 | 10/1974 | Acres | 252/432 |

Primary Examiner—Delbert E. Gantz
Assistant Examiner—G. E. Schmitkons
Attorney, Agent, or Firm—James R. Hoatson, Jr.; Thomas K. McBride; William H. Page II

[57] ABSTRACT

Dehydrocyclizable hydrocarbons are converted to aromatics by contacting them at dehydrocyclization conditions with an acidic multi-metallic catalytic composite comprising a combination of catalytically effective amounts of a platinum or palladium component, a rhodium component, a nickel component, and a halogen component with a porous carrier material. In a preferred embodiment, the catalytic composite also contains a catalytically effective amount of a Group IVA metallic component. The platinum or palladium, rhodium, nickel and halogen components are present in the multimetallic catalyst in amounts respectively, calculated on an elemental basis, corresponding to about 0.01 to about 2 wt. % platinum or palladium metal, about 0.01 to about 2 wt. % rhodium, about 0.01 to about 5 wt. % nickel, and about 0.1 to about 3.5 wt. % halogen. Moreover, the catalytically active sites induced by these metallic components are uniformly dispersed throughout the porous carrier material and these metallic components are present in the catalyst in carefully controlled oxidation states such that substantially all of the platinum or palladium, rhodium and nickel components are in the elemental metallic state. A specific example of dehydrocyclization method disclosed herein is a method for converting a feed mixture of n-hexane and n-heptane to a product mixture of benzene and toluene which involves contacting the feed mixture and a hydrogen stream with the acidic multimetallic catalyst disclosed herein at dehydrocyclization conditions.

25 Claims, No Drawings

DEHYDROCYCLIZATION WITH AN ACIDIC MULTIMETALLIC CATALYTIC COMPOSITE

CROSS-REFERENCE TO RELATED APPLICATIONS

This application is a continuation-in-part of my prior, copending application Ser. No. 490,171 filed July 19, 1974 (now U.S. Pat. No. 3,948,762). All of the teachings of this prior application are specifically incorporated herein by reference. The subject of the present invention is, broadly, an improved method for dehydrocyclizing a dehydrocyclizable hydrocarbon to produce an aromatic hydrocarbon. In a narrower aspect, the present invention involves a method dehydrocyclizing aliphatic hydrocarbons containing 6 to 20 carbon atoms per molecule to monocyclic aromatic hydrocarbons with minimum production of side products such as $C_1$ to $C_5$ hydrocarbons, bicyclic aromatics, olefins and coke. In another aspect, the present invention relates to the dehydrocyclization use of an acidic multimetallic catalytic composite comprising a combination of catalytically effective amounts of a platinum or palladium component, a rhodium component, a nickel component, and a halogen component with a porous carrier material. This acidic multimetallic composite has been found to possess highly beneficial characteristics of activity, selectivity, and stability when it is employed in the dehydrocyclization of dehydrocyclizable hydrocarbons to make aromatics such as benzene, toluene and xylene.

The conception of the present information followed from my search for a novel catalytic composite possessing a hydrogenation-dehydrogenation function, a controllable cracking and isomerization function, and superior conversion, selectivity, and stability characteristics when employed in hydrocarbon conversion processes that have traditionally utilized dual-function catalytic compsites. In my prior applications, I disclosed a significant finding with respect to a multimetallic catalytic composite meeting these requirements. More specifically, I determined that a combination of specified amounts of a rhodium component and a nickel component can be utilized, under certain conditions, to beneficially interact with the platinum or palladium component of a dual-function acidic catalyst with a resultant marked improvement in the performance of such a catalyst. Now I have ascertained that an acidic multimetallic catalystic composite, comprising a combination of catalytically effective amounts of a platinum or palladium component, a rhodium component, a nickel component and a halogen component with a porous carrier material, can have superior activity, selectivity, and stability characteristics when it is employed in a ring-closure or dehydrocyclization process if the catalytically active sites induced by these components are uniformly dispersed in the porous carrier material in the amounts specified hereinafter and if the oxidation state of the active metallic ingredients are carefully controlled so that substantially all of the platinum or palladium, rhodium and nickel components are present in the elemental metalic state. Moreover, in a particularly preferred embodiment of the present invention, this acidic multimetallic catalytic composite also contains a catalytically effective amount of a Group IVA metallic component which is maintained therein in a positive oxidation state.

The dehydrocyclization of dehydrocyclizable hydrocarbons is an improtant commercial process because of the great and expanding demand for aromatic hydrocarbons for use in the manufacture of various chemical products such as synthetic fibers, insecticides, adhesives, detergents, plastics, synthetic rubbers, pharmaceutical products, high octane gasoline, perfumes, drying oils, ion-exchange resins, and various other products well known to those skilled in the art. One example of this demand is in the manufacture of alkylated aromatics such as ethylbenzene, cumene and dodecylbenzene by using the appropriate mono-olefins to alkylate benzene. Another example of this demand is in the area of chlorination of benzene to give chlorobenzene which is then used to prepare phenol by hydrolysis with sodium hydroxide. The chief use for phenol is of course in the manufacture of phenol-formaldehyde resins and plastics. Another route to phenol uses cumene as a starting material and involves the oxidation of cumene by air to cumene hydroperoxide which can then be decomposed to phenol and acetone by the action of an appropriate acid. The demand for ethylbenzene is primarily derived from its use to manufacture styrene by selective dehydrogenation; styrene is in turn used to make styrenebutadiene rubber and polystyrene. Orthoxylene is typically oxidized to phthalic anhydride by reaction in vapor phase with air in the presence of a vanadium pentoxide catalyst. Phthalic anhydride is in turn used for production of plasticizers, polyesters and resins. The demand for paraxylene is caused primarily by its use in the manufacture of terephthalic acid or dimethyl terephthalate which in turn is reacted with ethylene glycol and polymerized to yield polyester fibers. Substantial demand for benzene also is associated with its use to produce aniline, Nylon, maleic anhydride, solvents and the like petrochemical products. Toluene, on the other hand, is not, at least relative to benzene and the $C_8$ aromatics, in great demand in the petrochemical industry as a basic building block chemical; consequently, substantial quantities of toluene are hydrodealkylated to benzene or disproportionated to benzene and xylene. Another use for toluene is associated with the transalkylation of trimethylbenzene with toluene to yield xylene.

Responsive to this demand for these aromatic products, the art has developed a number of alternative methods to produce them in commercial quantities. One method that has been widely studied involves the selective dehydrocyclization of a dehydrocyclizable hydrocarbon by contacting the hydrocarbon with a suitable catalyst at dehydrocyclization conditions. As is the case with most catalytic procedures, the principal measure of effectiveness for this dehydrocyclization method involves the ability to perform its intended function with minimum interference of side reactions for extended periods of time. The analytical terms used in the art to broadly measure how well a particular catalyst performs its intended functions in a particular hydrocarbon conversion reaction are activity, selectivity, and stability, and for purposes of discussion here, these terms are generally defined for a given reactant as follows: (1) activity is a measure of the catalyst's ability to convert the hydrocarbon reactant into products at a specified severity level where severity level means the specific reaction conditions used —— that is, the temperature, pressure, contact time, and presence of diluents such as $H_2$; (2) selectivity usually refers to the amount of desired product or products obtained relative to the amount of the reactant charged or converted; (3) stability refers to the rate of change with time of the activity and selectivity parameters — — obviously the smaller rate implying the more stable catalyst. More specifically, in a dehydrocyclization process, activity commonly refers to the amount of conversion that takes place for a given dehydrocyclizable hydrocarbon at a specified severity level and is typically measured on the basis of disappearance of the dehydrocyclizable hydrocarbon; selectivity is typically measured by the amount, calculated on a weight percent of feed basis or on a mole percent of converted dehydrocyclizable hydrocarbon basis, of the desired aromatic hydrocarbon or hydrocarbons obtained at the particular activity or severity level; and stability is typically equated to the rate of change with time of activity as measured by disappearance of the dehydrocyclizable hydrocarbon and of selectivity as measured by the amount of desired aromatic hydrocarbon produced. Accordingly, the major problem facing workers in the hydrocarbon dehydrocyclization or ring-closure art is the development of a more active and selective catalytic composite that has good stability characteristcs.

I have now found a dual-function acidic multimetallic catalytic composite which possesses improved activity, selectivity, and stability when it is employed in a process for the dehydrocyclization of dehydrocyclizable hydrocarbons. In particular, I have determined that the use of an acidic multimetallic catalyst, comprising a combination of catalytically effective amounts of a platinum or palladium component, a rhodium component, a nickel component, and a halogen component with a porous refractory carrier material, can enable the performance of a dehydrocyclization process to be substantially improved if the catalytically active sites induced by the metallic components are uniformly dispersed throughout the carrier material in the amounts and relative relationships specified hereinafter and if their oxidation states of the active metallic ingredients are carefully controlled to be in the states hereinafter specified. Moreover, particularly good results are obtained when this catalyst also contains a catalytically effective amount of Group IVA metallic component. This acidic multimetallic catalytic composite is particularly useful in the dehydrocyclization of $C_6$ to $C_{10}$ paraffins to produce aromatic hydrocarbons such as benzene, toluene, and the xylenes with minimization of by-products such as $C_1$ to $C_5$ saturated hydrocarbons, bicylic aromatics, olefins and coke.

In sum, the current invention involves the significiant finding that a combination of a rhodium component and a nickel component can be utilized under the circumstances specified herein to beneficially interact with and promote an acidic dehydrocyclization catalyst containing a platinum or palladium component and, in the preferred case, a Group IVA metallic component, when it is used in the production of aromatics by ring-closure of aliphatic hydrocarbons.

It is, accordingly, one object of the present invention to provide a novel method for the dehydrocyclization of dehydrocyclizable hydrocarbons utilizing an acidic multimetalic catalytic composite comprising catalytically effective amounts of a platinum or palladium component, a rhodium component, a nickel component and a halogen component combined with a porous carrier material. A second object is to provide a novel acidic catalytic composite having superior performance characteristics when utilized in a dehydrocyclization process. Another object is to provide an improved method for the dehydrocyclization of paraffin hydrocarbons to produce aromatic hydrocarbons which method minimizes undesirable by-products such as $C_1$ to $C_5$ saturated hydrocarbons, bicyclic aromatics, olefins and coke.

In brief summary, one embodiment of the present invention involves a method for dehydrocyclizing a dehydrocyclizable hydrocarbon which comprises contacting the hydrocarbon at dehydrocyclization conditions with an acidic multimetallic catalytic composite comprising a porous carrier material containing a uniform dispersion of catalytically effective amounts of a platinum or palladium component, a rhodium component, a nickel component, and a halogen component. Moreover, substantially all of the platinum or palladium, rhodium and nickel components are present in the composite in the elemental metallic state. Futher these components are present in this composite in amounts, calculated on an elemental basis, sufficient to result in the composite containing about 0.01 to about 2 wt. % platinum or palladium metal, about 0.01 to about 2 wt. % rhodium, about 0.01 to about 5 wt. % nickel and about 0.1 to about 3.5 wt. % halogen.

A second embodiment relates to the dehydrocyclization method described in the first embodiment wherein the dehydrocyclizable hydrocarbon is aliphatic hydrocarbon containing 6 to 20 carbon atoms per molecule.

A highly preferred embodiment comprehends the dehydrocyclization method characterized in the first embodiment wherein the catalyst also contains about 0.01 to about 5 wt. % Group IVA metal and wherein substantially all of the Group IVA metal is present in an oxidation state above that of the elemental metal.

Another embodiment relates to the catalytic composite used in the first, second or third embodiments and involves the further limitation that the halogen component is combined chloride.

Other objects and embodiments of the present invention involve specific details regarding essential and preferred catalytic ingredients, preferred amounts of ingredients, suitable methods of multimetallic composite preparation, suitable dehydrocyclizable hydrocarbons, operating conditions for use in the dehydrocyclization process, and the like particulars. These are hereinafter given in the following detailed discussion of each of these facets of the present invention.

Regarding the dehydrocyclizable hydrocarbon that is subjected to the method of the present invention, it can in general be any aliphatic hydrocarbon or substituted aliphatic hydrocarbon capable of undergoing ring-closure to produce an aromatic hydrocarbon. That is, it is intended to include within the scope of the present invention, the dehydrocyclization of any organic compound capable of undergoing ring closure to produce an aromatic hydrocarbon containing the same, or less than the same, number of carbon atoms than the reactant compound and capable of being vaporized at the dehydrocyclization temperatures used herein. More particularly, suitable dehydrocyclizable hydrocarbons are: aliphatic hydrocarbons containing 6 to 20 carbon atoms per molecule such as $C_6$ to $C_{20}$ paraffins, $C_6$ to $C_{20}$ olefins and $C_6$ to $C_{20}$ polyolefins. Specific examples of suitable dehydrocyclizable hydrocarbons are: (1) paraffins such as n-hexane, 2-methylpentane, 3-methylpentane, 2,2-dimethylbutane, n-heptane, 2-methylhexane, 3-ethylpentane, 2,2-dimethylpentane, n-octane, 2-methylheptane, 3-ethylhexane, 2,2-dimethylhexane, 2,-methyl-3-ethylpentane, 2,2,3-trimethylpentane, n-nonane, 2-methyloctane, 2,2-dimethylheptane, n-decane and the like compounds; (2) olefins such as 1-hexene, 2-methyl-1-pentene, 1-heptene, 1-octene, 1-nonene and the like compounds; and, (3) diolefins such as 1,5-hexadiene, 2-methyl-2,4-hexadiene, 2,6-octadiene and the like diolefins.

In a preferred embodiment, the dehydrocyclizable hydrocarbon is a paraffin hydrocarbon having about 6 to 10 carbon atoms per molecule. For example, paraffin hydrocarbons containing about 6 to 8 carbon atoms per molecule are dehydrocyclized by the subject method to produce the corresponding aromatic hydrocarbon. It is to be understood that the specific dehydrocyclizable hydrocarbons mentioned above can be charged to the present method individually, in admixture with one or more of the other dehydrocyclizable hydrocarbons, or in admixture with other hydrocarbons such as naphthenes, aromatics, $C_1$ to $C_5$ paraffins and the like. Thus mixed hydrocarbon fractions, containing significiant quantities of dehydrocyclizable hydrocarbons that are commonly available in a typical refinery, are suitable charge stocks for the instant method; for example highly paraffinic straight run naphthas, paraffinic raffinates from aromatic extraction or adsorption, $C_6$ to $C_9$ paraffin-rich streams and the like refinery streams. Generally, best results are obtained with a charge stock comprising a mixture of $C_6$ to $C_9$ paraffins, and especially $C_6$ to $C_9$ normal paraffins. The charge stock for the present method is most commonly a paraffinic-rich naphtha fraction boiling in the range of about 140° to about 400° F.

The acidic multimetallic catalyst used in the present dehydrocyclization method comprises a porous carrier material having combined therewith catalytically effective amounts of a platinum or a palladium component, a rhodium component, a nickel component, a halogen component and, in an especially preferred embodiment, a Group IVA metallic component.

Considering first the porous carrier material utilized in the present invention, it is preferred that the material be a porous, adsorptive, high-surface area support having a surface area of about 25 to about 500 $m^2/g$. The porous carrier material should be relatively refractory to the conditions utilized in the hydrocarbon conversion process, and it is intended to include within the scope of the present invention carrier materials which have traditionally been utilized in dual-function hydrocarbon conversion catlysts such as: (1) activated carbon, coke, or charcoal; (2) silica or silica gel, silicon carbide, clays, and silicates including those synthetically prepared and naturally occurring, which may or may not be acid treated for example, attapulgus clay, china clay, diatomaceous earth, fuller's earth, kaolin, kieselguhr, etc.; (3) ceramics, porcelain, crushed firebrick, bauxite; (4) refractory inorganic oxides such as alumina, titanium dioxide, zirconium dioxide, chromium oxide, beryllium oxide, vanadium oxide, cesium oxide, hafnium oxide, zinc oxide, magnesia, boria, thoria, silica-alumina, silica-magnesia, chromia-alumina, alumina-boria, silica-zirconia, etc.; (5) crystalline zeolitic alumino silicates such as naturally occurring or synthetically prepared mordenite and/or faujasite, either in the hydrogen form or in a form which has been treated with multivalent cations; (6) spinels such as $MgAl_2O_4$, $FeAl_2O_4$, $ZnAl_2O_4$, $CaAl_2O_4$, and other like compounds having the formula $MO.Al_2O_3$ where M is a metal having a valence of 2; and (7) combinations of elements from one or more of these groups. The preferred porous carrier materials for use in the present invention are refractory inorganic oxides, with best results obtained with an alumina carrier material. Suitable alumina materials are the crystalline aluminas known as gamma-, eta-, and theta-alumina, with gamma- or eta-alumina giving best results. In addition, in sme embodiments the alumina carrier material may contain minor proportions of other well-known refractory inorganic oxides such as silica, zirconia, magnesia, etc.; however, the preferred support is substantially pure gamma- or eta-alumina. Preferred carrier materials have an apparent bulk density of about 0.3 to about 0.8 g/cc and surface area characteristics such that the average pore diameter is about 20 to 300 Angstroms, the pore volume is about 0.1 to about 1 cc/g and the surface area is about 100 to about 500 $m^2/g$. In general, best results are typically obtained with a gamma-alumina carrier material which is used in the form of spherical particles having: a relatively small diameter (i.e. typically about 1/16 inch), an apparent bulk density of abot 0.3 to about 0.8 g/cc, a pore volume of about 0.4 ml/g, and a surface area of about 150 to about 250 $m^2/g$.

The preferred alumina carrier material may be prepared in any suitable manner and may be synthetically prepared or natural occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide, to a salt of aluminum such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, tablets, etc., and utilized in any desired size. For the purpose of the present invention a particularly preferred form of alumina is the sphere, and alumina spheres may be continuously manufactured by the well-known oil drop method which comprises: forming an alumina hydrosol by any of the techniques taught in the art and preferably by reacting aluminum metal with hydrochloric acid, combining the resultant hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300°. to about 400° F. and subjected to a calcination procedure at a temperature of about 850°. to about 1300° F. for a period of about 1 to about 20 hours. This treatment effects conversion of the alumina hydrogel to the corresponding crystalline gamma-alumina. See the teachings of U.S. Pat. No. 2,620,314 for additional details.

One essential ingredient of the present catalytic composite is a nickel component. This component may be present in the composite as an elemental metal, or in chemical combinations with one or more of the other ingredients of the composite, or as a chemical compound of nickel such as nickel oxide, sulfide, halide, oxychloride, aluminate and the like. Best results are obtained when the composite contains substantially all of this component in the elemental state, and the preferred preparation procedure which is given in Example I is believed to result in this condition. The nickel component may be utilized in the composite in any amount which is catalyticaly effective, with the preferred amount being about 0.01 to about 5 wt. % thereof, calculated on an elemental nickel basis. Typically, best results are obtained with about 0.05 to about 2 wt. % nickel. It is, additionally, preferred to select the specific amount of nickel from within this broad weight range as a function of the amount of the platinum or palladium component, on an atomic basis, as is explained hereinafter.

The nickel component may be incorporated into the catalytic composite in any suitable manner known to those skilled in the catalyst formulation art. In addition, it may be added at any stage of the preparation of the composite — either during preparation of the carrier material or thereafter — since the precise method of incorporation used is not deemed to be critical. However, best results are thought to be obtained when the nickel component is relatively uniformly distributed throughout the carrier material, and the preferred procedures are the ones that are known to result in a composite having a relatively uniform distribution. One acceptable procedure for incorporating this component into the composite involves cogelling the nickel component during the preparation of the preferred carrier material, alumina. This procedure usually comprehends the addition of a soluble, decomposable compound of nickel such as nickel chloride to the alumina hydrosol before it is gelled. The resulting mixture is then finished by conventional gelling, aging, drying, and calcination steps as explained hereinbefore. One preferred way of incorporating this component is an impregnation step wherein the porous carrier material is impregnated with a suitable nickel-containing solution either before, during, or after the carrier material is calcined. preferred impregnation solutions are aqueous solutions of water-soluble, decomposable nickel compounds such as nickel bromate, nickel bromide, nickel perchlorate, nickel chloride, nickel fluoride, nickel iodide, nickel nitrate, nickel sulfate, and the like compounds. Best results are ordinarily obtained when the impregnation solution is an aqueous solution of nickel chloride or nickel nitrate. This nickel component can be added to the carrier material, either prior to, simultaneously with, or after the other metallic components are combined therewith. Best results are usually achieved when this component is added simultaneously with the other metallic components. In fact, excellent results are obtained, as reported in the examples, with a one step inpregnation procedure using an aqueous solution comprising chloroplatinic acid, nickel chloride, hydrochloric acid, and rhodium trichloride hydrate.

A second essential ingredient of the subject catalyst is the platinum or palladium component. That is, it is intended to cover the use of platinum or palladium or mixtures thereof as a second component of the present composite. It is an essential feature of the present invention that substantially all of this platinum or palladium component exists within the final catalytic composite in the elemental metallic state. Generally, the amount of this component present in the final catalyst composite is small compared to the quantities of the other components combined therewith. In fact, the platinum or palladium component generally will comprise about 0.01 to about 2 wt. % of the final catalytic composite, calculated on an elemental basis. Excellent results are obtained when the catalyst contains about 0.05 to about 1 wt. % of platinum or palladium metal.

This platinum or palladium component may be incorporated in the catalytic composite in any suitable manner known to result in a relatively uniform distribution of this component in the carrier material such as coprecipitation or cogelation, ion exchange or impregnation. The preferred method of preparing the catalyst involves the utilization of a soluble, decomposable compound of platinum or palladium to impregnate the carrier material in a relatively uniform manner. For example, this component may be added to the support by commingling the latter with an aqueous solution of chloroplatinic or chloropalladic acid. Other water-soluble compounds of platinum or palladium may be employed in impregnation solutions and include ammonium chloroplatinate, bromoplatinic acid, platinum trichloride, platinum tetrachloride hydrate, platinum dichlorocarbonyl dichloride, dinitrodiaminoplatinum, sodium tetranitroplatinate (II), palladium chloride, palladium nitrate, palladium sulfate, diamminepalladium (II) hydroxide, tetramminepalladium (II) chloride, etc. The utilization of a platinum or palladium chloride compound, such as chloroplatinic or chloropalladic acid, is preferred since it facilitates the incorporation of both the platinum or palladium component and at least a minor quantity of the halogen component in a single step. Hydrogen chloride or the like acid is also generally added to the impregnation solution in order to further facilitate the incorporation of the halogen component and the uniform distribtion of the metallic components throughout the carrier material. In addition it is generally preferred to impregnate the carrier material after it has been calcined in order to minimize the risk of washing away the valuable platinum or palladium compounds; however,in some cases, it may be advantageous to impregnate the carrier material when it is in a gelled state.

Yet another essential ingredient of the present catalytic composite is a rhodium component. It is of fundamental importance that substantially all of the rhodium component exists within the catalytic composite of the present invention in the elemental metallic state and the subsequently described reduction procedure is designed to accomplish this objective. The rhodium component may be utilized in the composite in any amount which is catalytically effective, with the preferred amount being about 0.01 to about 2 wt. % thereof, calculated on an elemental basis. Typically, best results are obtained with about 0.05 to about 1 wt. % rhodium. It is additionally preferred to select the specific amount of rhodium from within this broad weight range as a function of the amount of the platinum or palladium component, on an atomic basis, as is explained hereinafter.

This rhodium component may be incorporated into the catalytic composite in any suitable manner known to those skilled in the catalyst formulation art which results in a relatively uniform dispersion of rhodium in the carrier material. In addition, it may be added at any stage of the preparation of the composite — either during preparation of the carrier material or thereafter — and the precise method of incorporation used is not deemed to be critical. However, best results are obtained when the rhodium component is relatively uniformly distributed throughout the carrier material, and the preferred procedures are the ones known to result in a composite having this relatively uniform distribution. One acceptable procedure for incorporating this component into the composite involves cogelling or coprecipitating the rhodium component during the preparation of the preferred carrier material, alumina. This procedure usually comprehends the addition of a soluble, decomposable compound of rhodium such as rhodium trichloride hydrate to the alumina hydrosol before it is gelled. The resulting mixture is then finished by conventional gelling, aging, drying, and calcination steps as explained hereinbefore. A preferred way of incorporating this component is an impregnation step wherein the porous carrier material is impregnated with a suitable rhodium-containing solution either before, during, or after the carrier material is calcined. Preferred impregnation solutions are aqueous solutions of water soluble, decomposable rhodium compounds such as hexamminerhodium chloride, rhodium carbonylchloride, rhodium trichloride hydrate, rhodium nitrate, sodium hexachlororhodate (III), sodium hexanitrorhodate (III), rhodium sulfate, and the like compounds. Best results are ordinarily obtained when the impregnation solution is an aqueous solution of rhodium trichloride hydrate or rhodium nitrate. This component can be added to the carrier material, either prior to, simultaneously with, or after the other metallic components are combined therwith. Best results are usually achieved when this component is added simultaneously with the other metallic components. In fact, excellent results are obtained, as reported in the examples, with a one step impregnation procedure using an aqueous solution comprising chloroplatinic or chloropalladic acid, rhodium trichloride, hydrochloric acid, and nickel chloride or nitrate.

It is essential to incorporate a halogen component into the acidic multimetallic catalytic composite used in the present invention. Although the precise form of the chemistry of the association of the halogen component with the carrier material is not entirely known, it is customary in the art to refer to the halogen component as being combined with the carrier material, or with the other ingredients of the catalyst in the form of the halide (e.g. as the chloride). This combined halogen may be either fluorine, chlorine, iodine, bromine, or mixtures thereof. Of these, fluorine and, particularly, chlorine are preferred for the purposes of the present invention. The halogen may be added to the carrier material in any suitable manner, either during preparation of the support or before or after the addition of the other components. For example, the halogen may be added, at any stage of the preparation of the carrier material or to the calcined carrier material, as an aqueous solution of a suitable, decomposable halogen-containing compound such as hydrogen fluoride, hydrogen chloride, hydrogen bromide, ammonium chloride, etc. The halogen component or a portion thereof, may be combined with the carrier material during the impregnation of the latter with the platinum or palladium and rhodium components; for example, through the utilization of a mixture of chloroplatinic acid and hydrogen chloride. In another situation, the alumina hydrosol which is typically utilized to form the preferred alumina carrier material may contain halogen and thus contribute at least a portion of the halogen component to the final composite. For the dehydrocyclization reaction, the halogen will be typically combined with the carrier material in an amount sufficient to result in a final composite that contains about 0.1 to about 3.5%, and preferably about 0.5 to about 1.5% by weight of halogen, calculated on an elemental basis. It is to be understood that the specified level of halogen component in the instant catalyst can be achieved or maintained during use in the dehydrocyclization of hydrocarbons by continuously or periodically adding to the reaction zone a decomposable halogen-containing compound such as an organic chloride (e.g. ethylene dichloride, carbon tetrachloride, t-butyl chloride) in an amount of about 1 to 100 wt. ppm. of the hydrocarbon feed, and preferably about 1 to 10 wt. ppm.

One especially preferred constituent of the instant acidic multimetallic catalytic composite is a Group IVA metallic component. By the use of the generic term "Group IVA metallic component" it is intended to cover the metals of Group IVA of the Periodic Table. More specifically, it is intended to cover: germanium, tin, lead, and mixtures of these metals. It is essential that substantially all of the Group IVA metallic component is present in the final catalyst in an oxidation state above that of the elemental metal. In other words, this component may be present in chemical combination with one or more of the other ingredients of the composite, or as a chemical compound of the Group IVA metal such as the oxide, sulfide, halide, oxyhalide, oxychloride, aluminate, and the like compounds. Based on the evidence currently available, it is believed that best results are obtained when substantially all of the Group IVA metallic component exists in the final composite in the form of the corresponding oxide such as the tin oxide, germanium oxide, and lead oxide, and the subsequently described oxidation and reduction steps, that are preferably used in the preparation of the instant composite, are believed to result in a catalytic composite which contains an oxide of the Group IVA metallic component. Regardless of the state in which this component exists in the composite, it can be utilized therein in any amount which is catalytically effective, with the preferred amount being about 0.01 to about 5 wt. % thereof, calculated on an elemental basis and the most preferred amount being about 0.05 to about 2 wt. %. The exact amount selected within this broad range is preferably determined as a function of the particular Group IVA metal that is utilized. For instance, in the case where this component is lead, it is preferred to select the amount of this component from the low end of this range — namely, about 0.01 to about 1 wt. %. Additionally, it is preferred to select the amount of lead as a function of the amount of the platinum group component as explained hereinafter. In the case where this component is tin, it is preferred to select from a relatively broader range of about 0.05 to about 2 wt. % thereof. And, in the preferred case, where this component is germanium the selection can be made from the full breadth of the stated range — specifically, about 0.01 to about 5 wt. %, with best results at about 0.05 to about 2 wt. %.

This Group IVA component may be incorporated in the composite in any suitable manner known to the art to result in a uniform dispersion of the Group IVA moiety throughout the carrier material such as, coprecipitation or cogelation with the porous carrier material, ion exchange with the carrier material, or impregnation of the carrier material at any stage in its preparation. It is to be noted that it is intended to include within the scope of the present invention all conventional procedures for incorporating a metallic component in a catalytic composite, and the particular method of incorporation used is not deemed to be an essential feature of the present invention so long as the Group IVA component is uniformly distributed throughout the porous carrier material. One acceptable method of incorporating the Group IVA component into the catalytic composite involves cogelling the Group IVA component during the preparation of the preferred carrier material, alumina. This method typically involves the addition of a suitable compound of the Group IVA metal of interest to the alumina hydrosol. The resulting mixture is then commingled with a suitable gelling agent, such as a relatively weak alkaline reagent, and the resulting mixture is thereafter preferably gelled by dropping into a hot oil bath as explained hereinbefore. After aging, drying, and calcining the resulting particles, there is obtained an intimate combination of the oxide of the Group IVA metal and alumina. One preferred method of incorporating this component into the composite involves utilization of a soluble decomposable compound of the particular Group IVA metal of interest to impregnate the porous carrier material either before, during, or after the carrier material is calcined. In general, the solvent used during this impregnation step is selected on the basis of its capability to dissolve the desired Group IVA compound without affecting the porous carrier material which is to be impregnated; ordinarily, good results are obtained when water is the solvent; thus the preferred Group IVA compounds for use in this impregnation step are typically water-soluble and decomposable. Examples of suitable Group IVA compounds are: germanium difluoride, germanium tetra-alkoxide, germanium dioxide, germanium tetrafluoride, germanium monosulfide, tin chloride, tin bromide, tin dibromdie di-iodide, tin dichloride di-iodide, tin chromate, tin difluoride, tin tetraiodide, tin sulfate, tin tartate, lead acetate, lead bromate, lead bromide, lead chlorate, lead chloride, lead citrate, lead formate, lead lactate, lead malate, lead nitrate, lead nitrite, lead dithionate, and the like compounds. In the case where the Group IVA component is germanium, a preferred impregnation solution is germanium tetrachloride dissolved in anhydrous alcohol. In the case of tin, tin chloride dissolved in water is preferred. In the case of lead, lead nitrate dissolved in water is preferred. Regardless of which impregnation solution is utilized, the Group IVA component can be impregnated either prior to, simultaneously with, or after the other metallic components are added to the carrier material. Ordinarily, best results are obtained when this component is impregnated simultaneously with the other metallic components of the composite. Likewise, best results are ordinarily obtained when the Group IVA component is germanium oxide or tin oxide.

Regardless of which Group IVA compound is used in the preferred impregnation step, it is essential that the Group IVA metallic component be uniformly distributed throughout the carrier material. In order to achieve this objective when this component is incorporated by impregnation, it is necessary to maintain the pH of the impregnation solution at a relatively low level corresponding to about 7 to about 1 or less and to dilute the impregnation solution to a volume which is at least approximately the same or greater than the void volume of the carrier material which is impregnated. It is preferred to use a volume ratio of impregnation solution to void volume of carrier material of at least 1:1 and preferably about 2:1 to about 10:1 or more. Similarly, it is preferred to use a relatively long contact time during the impregnation step ranging from about ¼ hour up to about ½ hour or more before drying to remove excess solvent in order to insure a high dispersion of the Group IVA metallic component in the carrier material. The carrier material is, likewise, preferably constantly agitated during this preferred impregnation step.

Regarding the preferred amounts of the various metallic components of the subject catalyst, I have found it to be a good practice to specify the amounts of the rhodium, nickel, and the Group IVA metallic components as a function of the amount of the platinum or palladium component. On this basis, the amount of the rhodium component is ordinarily selected so that the atomic ratio of rhodium to platinum or palladium metal contained in the composite is about 0.1:1 to about 2:1, with the preferred range being about 0.25:1 to about 1.5:1. Similarly, the amount of the nickel component is ordinarily selected to produce a composite containing an atomic ratio of nickel to platinum or palladium metal of about 0.2:1 to about 20:1, with the preferred range being about 1:1 to about 10:1. The amount of preferred Group IVA metallic component is likewise selected so that the atomic ratio of Group IVA metal to platinum or palladium is 0.05:1 to about 10:1, with best results obtained when this ratio is fixed on the basis of the individual Group IVA species as follows: (1) for germanium, it is about 0.3:1 to 10:1 and most preferably about 0.6:1 to 6:1, (2) for tin, it is about 0.1:1 to 3:1 and most preferably about 0.5:1 to 1.5:1; and (3) for lead, it is about 0.05:1 to 0.9:1 and most preferably about 0.1:1 to 0.75:1.

Another significant parameter for the instant catalyst is the "total metals content" which is defined to be the sum of the platinum or palladium component, the rhodium component, the nickel component, and the Group IVA metallic component (when it is present), calculated on an elemental basis. Good results are ordinarily obtained with the subject catalyst when this parameter is fixed at a valve of about 0.15 to about 3 wt. %, with best results ordinarily achieved at a metals loading of about 0.3 to about 2 wt. %.

Regardless of the details of how the components of the catalyst are combined with the porous carrier material, the final catalyst generally will be dried at a temperature of about 200° to about 600° F. for a period of at least about 2 to about 24 hours or more, and finally calcined or oxidized at a temperature of about 700° to about 1100° F. in an air or oxygen atmosphere for a period of about 0.5 to about 10 hours in order to convert substantially all of the metallic components substantially to the oxide form. Because a halogen component is utilized in the catalyst, best results are generally obtained when the halogen content of the catalyst is adjusted during the oxidation step by including a halogen, hydrogen halide, or a halogen-containing compound which decomposes to yield a hydrogen halide in the air or oxygen atmosphere utilized. In particular, when the halogen component of the catalyst is chlorine, it is preferred to use a mole ratio of $H_2O$ to HCl of about 5:1 to about 100:1 during at least a portion of the oxidation step in order to adjust the final chlorine content of the catalyst to a range of about 0.1 to about 3.5 wt. %. Preferably, the duration of this halogenation step is about 1 to about 5 hours.

It is an essential feature of the present invention that the resultant oxidized catalytic composite is subjected to a substantially water-free and hydrocarbon-free reduction step prior to its use in the dehydrocyclization of hydrocarbons. This step is designed to selectively reduce the platinum or palladium, rhodium, and nickel components to the corresponding metals and to insure a uniform and finely divided dispersion of these metallic components throughout the carrier material, while maintaining the preferred Group IVA metallic component in a positive oxidation state. Preferably, a substantially pure and dry hydrogen stream (i.e. less than 20 vol. ppm. $H_2O$) is used as the reducing agent in this step. The reducing agent is contacted with the oxidized catalyst at conditions including a temperature of about 400° to about 1200° F. and a period of time of about 0.5 to 10 hours effective to reduce substantially all of the platinum or palladium, nickel, and rhodium components to their elemental metallic state, while maintaining the preferred Group IVA metallic component in an oxidation state above that of the elemental metal. This reduction treatment may be performed in situ as part of a start-up sequence if precautions are taken to predry the plant to a substantially water-free state and if substantially water-free and hydrocarbon-free hydrogen is used.

The resulting reduced catalytic composite may, in some cases, be beneficially subjected to a presulfiding operation designed to incorporate in the catalytic composite about 0.01 to 1, most preferably about 0.05 to 0.5 wt. % sulfur, calculated on an elemental basis. Preferably, this presulfiding treatment takes place in the presence of hydrogen and a suitable sulfur-containing decomposable compound such as hydrogen sulfide, lower molecular weight mercaptans, organic sulfides, etc. Typcially, this procedure comprises treating the selectively reduced catalyst with a sulfiding gas such as a mixture of hydrogen and hydrogen sulfide having about 10 moles of hydrogen per mole of hydrogen sulfide at conditons sufficient to effect the desired incorporation of sulfur, generally including a temperature ranging from about 50° up to about 1100° F. or more. It is generally a good practice to perform this presulfiding step under substantially water-free conditions. It is within the scope of the present invention to maintain or achieve the sulfided state of the instant catalyst during use in the conversion of hydrocarbons by continuously or periodically adding a decomposable sulfur-containing compound, such as the ones previously mentioned, to the reactor containing the catalyst in an amount sufficient to provide about 1 to 500 wt. ppm., preferably 1 to 20 wt. ppm. of sulfur based on hydrocarbon charge.

According to the present invention, the dehydrocyclizable hydrocarbon is contacted with the instant acidic multimetallic catalyst in a dehydrocyclization zone maintained at dehydrocyclization conditions. This contacting may be accomplished by using the catalyst in a fixed bed system, a moving bed system, a fluidized bed system, or in a batch type operation; however, in view of the danger of attrition losses of the valuable catalyst and of well-known operational advantages, it is preferred to use either a fixed bed system or a dense-phase moving bed system such as is shown in U.S. Pat. No. 3,725,249. It is also contemplated that the contacting step can be performed in the presence of a physical mixture of particles of the catalyst of the present invention and particles of a conventional dual-function catalyst of the prior art. In a fixed bed system, the dehydrocyclizable hydrocarbon-containing charge stock is preheated by any suitable heating means to the desired reaction temperature and then passed into a dehydrocyclization zone containing a fixed bed of the acidic multimetallic catalyst. It is of course, understood that the dehydrocyclization zone may be one or more separate reactors with suitable means therebetween to ensure that the desired conversion temperature is maintained at the entrance to each reactor. It is also important to note that the reactants may be contacted with the catalyst bed in either upward, downward, or radial flow fashion with the latter being preferred. In addition, the reactants may be in the liquid phase, a mixed liquid-vapor phase, or a vapor phase when they contact the catalyst, with best results obtained in the vapor phase. The dehydrocyclization system then preferably comprises a dehydrocyclization zone containing one or more fixed beds or dense-phase moving beds of the instant catalyst. In a multiple bed system, it is, of course, within the scope of the present invention to use the present catalyst in less than all of the beds with a conventional dualfunction catalyst being used in the remainder of the beds. This dehydrocyclization zone may be one or more separate reactors with suitable heating means therebetween to compensate for the endothermic nature of the dehydrocyclization reaction that takes place in each catalyst bed.

It is also generally preferred to utilize the present acidic multimetallic catalytic composite in a substantially water-free environment. Essential to the achievement of this condition in the dehydrocyclization zone is the control of the water level present in the charge stock and the diluent stream which is being charged to the zone. Best results are ordinarily obtained when the total amount of water entering the conversion zone from any source is held to a level less than 20 ppm. and preferably less than 5 ppm. expressed as weight of equivalent water in the charge stock. In general, this can be accomplished by careful control of the water present in the charge stock and in the diluent stream. The charge stock can be dried by using any suitable drying means known to the art, such as a conventional solid adsorbent having a high selectivity for water, for instance, sodium or calcium crystalline aluminosilicates, silica gel, activated alumina, molecular sieves, anhydrous calcium sulfate, high surface area sodium, and the like adsorbents. Similarly, the water content of the charge stock may be adjusted by suitable stripping operations in a fractionation column or like device. And in some cases, a combination of adsorbent drying and distillation drying may be used advantageously to effect almost complete removal of water from the charge stock. In an especially preferred mode of operation, the charge stock is dried to a level corresponding to less than 5 wt. ppm. of $H_2O$ equivalent. In general, it is preferred to maintain the diluent stream entering the hydrocarbon conversion zone at a level of about 10 vol. ppm. of water or less and most preferably about 5 vol. ppm. or less. If the water level in the diluent stream is too high, drying of same can be conveniently accomplished by contacting this stream with a suitable desiccant such as those mentioned above.

The dehydrocyclization conditions used in the present method include a reactor pressure which is selected from the range of about 0 psig. to about 250 psig., with the preferred pressure being about 50 psig. to about 150 psig. In fact, it is a singular advantage of the present invention that it allows stable operation at lower pressure than have heretofore been successfully utilized in dehydrocyclization system with all platinum monometallic catalysts. In other words, the acidic multimetallic catalyst of the present invention allows the operation of a dehydrocyclization system to be conducted at lower pressure for about the same or better catalyst cycle life before regeneration as has been heretofore realized with conventional monometallic catalysts at higher pressure.

The temperature required for dehydrocyclization with the instant catalyst is markedly lower than that required for a similar operation using a high quality catalyst of the prior art. This significant and desirable feature of the present invention is a consequence of the extraordinary activity of the acidic multimetallic catalyst of the present invention for the dehydrocyclization reaction. Hence, the present invention requires a temperature in the range of from 800° to about 1100° F. and preferably about 850° to about 1000° F. As is well known to those skilled in the dehydrocyclization art, the initial selection of the temperature within this broad range is made primarily as a function of the desired conversion level of the dehydrocyclizable hydrocarbon considering the characteristics of the charge stock and of the catalyst. Ordinarily, the temperature then is thereafter slowly increased during the run to compensate for the inevitable deactivation that occurs to provide a relatively constant value for conversion. Therefore, it is a feature of the present invention that not only is the initial temperature requirement substantially lower, but also the rate at which the temperature is increased in order to maintain a constant conversion level is substantially lower for the catalyst of the present invention than for an equivalent operation with a high quality dehydrocyclizaion catalyst which is manufactured in exactly the same manner as the catalyst of the present invention except for the inclusion of the rhodium and nickel components. Moreover, for the catalyst of the present invention, the aromatic yield loss for a given temperature increase is substantially lower than for a high quality dehydrocyclization catalyst of the prior art.

The liquid hourly space velocity (LHSV) used in the instant dehydrocyclization method is selected from the range of about 0.1 to about 5 hr. $^{-1}$, with a value in the range of about 0.3 to about 2 hr. $^{-1}$ being preferred. In fact, it is a feature of the present invention that it allows operations to be conducted at higher LHSV than normally can be stably achieved in a dehydrocyclization process with a high quality dehydrocyclization catalyst of the prior art. This last feature is of immense economic significance because it allows a dehydrocyclization process to operate at the same throughput level with less catalyst inventory or at greatly increased throughput level with the same catalyst inventory than that heretofore used with conventional dehydrocyclization catalysts at no sacrifice in catalyst life before regeneration.

Although hydrogen is the preferred diluent for use in the subject dehydrocyclization method, in some cases other art-recognized diluents may be advantageously utilized, either individually or in admixture with hydrogen, such as $C_1$ to $C_5$ paraffins such as methane, ethane, propane, butane and pentane; carbon dioxide, the like diluents, and mixtures thereof. Hydrogen is preferred because it serves the dual-function of not only lowering the partial pressure of the dehydrocyclizable hydrocarbon, but also of suppressing the formation of hydrogen-deficient, carbonaceous deposits (commonly called coke) on the catalytic composite. Ordinarily, hydrogen is utilized in amounts sufficient to insure a hydrogen to hydrocarbon mole ratio of about 0.1:1 to about 10:1, with best results obtained in the range of about 0.5:1 to about 5:1. The hydrogen stream charged to the dehydrocyclization zone will typically be recycle hydrogen obtained from the effluent stream from this zone after a suitable hydrogen separation step.

The following working examples are given to illustrate further the preparation of the acidic multimetallic catalytic composite used in the present invention and the beneficial use thereof in the dehydrocyclization of hydrocarbons. It is understood that the examples are intended to be illustrative rather than restrictive.

These examples are all performed in a laboratory scale dehydrocyclization plant comprising a reactor, a hydrogen separating zone, heating means, cooling means, pumping means, compressing means, and the like conventional equipment. In this plant, a sulfur-free feed stream containing the dehydrocyclizable hydrocarbon is combined with a hydrogen recycle stream and the resultant mixture heated to the desired conversion temperature, which refers herein to the temperature maintained at the inlet to the reactor. The heated mixture is then passed into contact with the instant acidic multimetallic catalyst which is maintained in a sulfur-free and water-free environment and which is present as a fixed bed of catalyst particles in the reactor. The pressures reported herein are recorded at the outlet from the reactor. An effluent stream is withdrawn from the reactor, cooled, and passed into the hydrogen-separating zone wherein a hydrogen-containing gas phase separates from a hydrocarbon-rich liquid phase containing aromatic hydrocarbons, unconverted dehydrocyclizable hydrocarbons, and by-prodicts of the dehydrocyclization reaction. A portion of the hydrogen-containing gas phase is recovered as excess recycle gas and the remaining portion is passed through a high surface area sodium scrubber and the resulting substantially water-free and sulfur-free hydrogen stream is recycled through suitable compressing means to the heating zone as described above. The hydrocarbon-rich liquid phase from the separating zone is withdrawn therefrom and subjected to analysis to determine conversion and selectivity for the desired aromatic hydrocarbon as will be indicated in the Examples. Conversion numbers of the dehydrocyclizable hydrocarbon reported herein are all calculated on the basis of disappearance of the dehydrocyclizable hydrocarbon and are expressed in weight percent. Similarly, selectivity numbers are reported on the basis of weight of desired aromatic hydrocarbon produced per 100 weight parts of dehydrocyclizable hydrocarbon charged.

All of the catalysts utilized in these examples are prepared according to the following general method with suitable modification in stoichiometry to achieve the compositions reported in each example. First, an alumina carrier material comprising 1/16 inch spheres having an apparent bulk density of about 0.5 g/cc is prepared by: forming an aluminum hydroxyl chloride sol by dissolving substantially pure aluminum pellets in a hydrochloric acid solution, adding hexamethylenetetramine to the resulting alumina sol, gelling the resulting solution by dropping it into an oil bath to form spherical particles of an alumina hydrogel; aging, and washing the resulting particles with an ammoniacal solution and finally drying and calcining the aged and washed particles to form spherical particles of gamma-alumina containing about 0.3 wt. % combined chloride. Additional details as to this method of preparing this alumina carrier material are given in the teachings of U.S. Pat. No. 2,620,314.

The resulting gamma-alumina particles are then contacted at suitable impregnation conditions with an aqueous impregnation solution containing chloroplatinic acid, rhodium trichloride hydrate, nickel chloride and hydrogen chloride. In the example where the catalyst contains a germanium component, an aged solution comprising germanium tetrachloride dissolved in anhydrous ethanol is added to this impregnation solution. The amounts of metallic reagents contained in this impregnation solution are carefully adjusted to yield a final multimetallic catalytic composite containing a uniform dispersion of the desired amounts of platinum, rhodium, nickel and germanium. The hydrochloric acid is utilized in an amount of about 3 wt. % of the alumina particles. In order to ensure a uniform dispersion of the metal moieties in the carrier material, the impregnation solution is maintained in contact with the carrier material particles for about ½ to about 3 hours at a temperature of about 70° F. with constant agitation. The impregnated spheres are then dried at a temperature of about 225° F. for about an hour and thereafter calcined or oxidized with a sulfur-free dry air stream at a temperature of about 975° F. and a GHSV of about 500 hr. $^{-1}$ for about ½ hour effective to convert substantially all of the metallic components to the corresponding oxide forms. In general, it is a good practice to thereafter treat the resulting oxidized particles with a sulfur-free air stream containing $H_2O$ and HCl in a mole ratio of about 30:1 at a temperature of about 975° F. for an additional period of about 2 hours in order to adjust the combined chloride contained in the catalyst to a value of about 1 wt. %. The halogen-treated spheres are next subjected to a second oxidation step with a dry sulfur-free air stream at 975° F. and a GHSV of 500 hr. $^{-1}$ for an additional period of about ½ hour. The resulting oxidized and halogen-treated particles are thereafter subjected to a dry prereduction treatment designed, as pointed out hereinbefore, to reduce substantially all of the platinum, rhodium and nickel components to the elemental metallic state, while maintaining the germanium component (if present) in a positive oxidation state. This step involves contacting the catalyst particles with a substantially sulfur-free and hydrocarbon-free hydrogen stream containing less than 5 vol. ppm. of $H_2O$ at a temperature of 1050° F., atmospheric pressure and a GHSV of about 400 hr. $^{-1}$ for a period of about 1 hour.

EXAMPLE I

The reactor is loaded with 100 cc of an acidic catalyst containing, on an elemental basis, 0.375 wt. % platinum, 0.25 wt. % rhodium, 0.25 wt. % nickel, 0.5 wt. % germanium and about 1 wt. % chloride. The feed stream utilized is commercial grade n-hexane. The feed stream is contacted with the catalyst at a temperature of 920° F., a pressure of 125 psig., a liquid hourly space velocity of 0.75 hr. $^{-1}$, and a hydrogen to hydrocarbon mole ratio of 3:1. The dehydrocyclization plant is lined-out at these conditions and a 20 hour test period commenced. The hydrocarbon product stream from the plant is continuously analyzed by GLC (gas liquid chromatography) and about a 90% conversion of n-hexane is observed with a selectivity for benzene of about 25%.

EXAMPLE II

The acidic catalyst contains, on an elemental basis, 0.375 wt. % platinum, 0.5 wt. % nickel, 0.1 wt. % rhodium and 1 wt. % combined chloride. The feed stream is commercial grade normal heptane. The dehydrocyclization reactor is operated at a temperature of 900° F., a pressure of 125 psig., a liquid hourly space velocity of 0.75 hr. $^{-1}$, and hydrogen to hydrocarbon mole ratio of 3:1. After a line-out period, a 20 hour test period is performed during which the average conversion of the n-heptane is maintained at about 95% with a selectivity for aromatics (a mixture of toluene and benzene) of about 45%.

EXAMPLE III

The acidic catalyst is the same as utilized in Example II. The feed stream is normal octane. The conditions utilized are a temperature of 880° F., a pressure of 125 psig., a liquid hourly space velocity of 0.75 hr. $^{-1}$, and a hydrogen to hydrocarbon mole ratio of 3:1. After a line-out period, a 20 hour test shows an average conversion of about 100% and a selectivity for aromatics of about 50%.

EXAMPLE IV

The acidic catalyst contains, on an elemental basis, 0.3 wt. % platinum, 1 wt. % nickel, 0.1 wt. % rhodium and 1 wt. % combined chloride. The feed stream is a 50/50 mixture of n-hexane and n-heptane. The conditions utilized are a temperature of 945° F., a pressure of 125 psig., a liquid hourly space velocity of 0.75 hr.$^{-1}$, and a hydrogen to hydrocarbon mole ratio of 2:1. After a line-out period, a 20 hour test is performed with a conversion of about 100% and a selectivity for aromatics of about 45%. The selectivity for benzene and toluene are about 20 and 25%, respectively.

It is intended to cover by the following claims, all changes and modifications of the above disclosure of the present invention which would be self-evident to a man of ordinary skill in the catalyst-formulation art or in the hydrocarbon dehydrocyclization art.

I claim as my invention:

1. A method for dehydrocyclizing a dehydrocyclizable hydrocarbon comprising contacting the hydrocarbon at dehydrocyclization conditions with an acidic catalytic composite comprising a porous carrier material containing, or an elemental basis, about 0.01 to about 2 wt. % platinum or palladium, about 0.01 to about 2 wt. % rhodium, about 0.01 to about 5 wt. % nickel and about 0.1 to about 3.5 wt. % halogen; wherein the platinum or palladium, rhodium and nickel are uniformly dispersed throughout the porous carrier material; and wherein substantially all of the platinum or palladium, rhodium and nickel are present in the elemental metallic state.

2. A method as defined in claim 1 wherein the dehydrocyclizable hydrocarbon is admixed with hydrogen when it contacts the catalytic composite.

3. A method as defined in claim 1 wherein the porous carrier material is a refractory inorganic oxide.

4. A method as defined in claim 3 wherein the refractory inorganic oxide is alumina.

5. A method as defined in claim 1 wherein the halogen is combined chloride.

6. A method as defined in claim 1 wherein the dehydrocyclizable hydrocarbon is an aliphatic hydrocarbon containing 6 to 20 carbon atoms per molecule.

7. A method as defined in claim 6 wherein the aliphatic hydrocarbon is an olefin.

8. A method as defined in claim 6 wherein the aliphatic hydrocarbon is a paraffin.

9. A method as defined in claim 8 wherein the paraffin hydrocarbon is a paraffin containing 6 to 10 carbon atoms per molecule.

10. A method as defined in claim 8 wherein the paraffin is hexane.

11. A method as defined in claim 8 wherein the paraffin is heptane.

12. A method as defined in claim 8 wherein the paraffin is octane.

13. A method as defined in claim 8 wherein the paraffin is nonane.

14. A method as defined in claim 8 wherein the paraffin is a mixture of $C_6$ to $C_9$ paraffins.

15. A method as defined in claim 1 wherein the dehydrocyclizable hydrocarbon is contained in a naphtha fraction boiling in the range of about 140° to about 400° F.

16. A method as defined in claim 2 wherein the dehydrocyclization conditions include a temperature of 800° to about 1100° F., a pressure of 0 to 250 psig., a LHSV of 0.1 to 5 hr.$^{-1}$, and a hydrogen to hydrocarbon mole ratio of about 0.1:1 to about 10:1.

17. A method as defined in claim 1 wherein the composite contains, on an elemental basis, about 0.05 to about 1 wt. % platinum or palladium, about 0.05 to about 1 wt. % rhodium and about 0.05 to about 2 wt. % nickel and about 0.5 to about 1.5 wt. % halogen.

18. A method as defined in claim 1 wherein the metals content of the catalytic composite is adjusted so that the atomic ratio of nickel to platinum or palladium is about 0.2:1 to about 20:1.

19. A method as defined in claim 1 wherein the metals content of the catalytic composite is adjusted so that the atomic ratio of rhodium to platinum or palladium is about 0.1:1 to about 2:1.

20. A method as defined in claim 1 wherein the contacting is performed in a substantially water-free environment.

21. A method as defined in claim 1 wherein the catalytic composite contains, on an elemental basis, about 0.01 to about 5 wt. % Group IVA metal and wherein substantially all of the Group IVA metal is present in an oxidation state above that of the elemental metal.

22. A method as defined in claim 21 wherein the Group IVA metal is germanium.

23. A method as defined in claim 21 wherein the Group IVA metal is tin.

24. A method as defined in claim 21 wherein the Group IVA metal is lead.

25. A method as defined in claim 21 wherein the Group IVA metal is present in the catalytic composite in the form of the corresponding oxide.

* * * * *